United States Patent [19]
Zindler et al.

[11] 3,960,498
[45] June 1, 1976

[54] ELECTROCHEMICAL ANALYSIS SYSTEM

[75] Inventors: Jerrold Zindler, Boston; Gustav H. Dreier, Acton, both of Mass.

[73] Assignee: Instrumentation Laboratory, Inc., Lexington, Mass.

[22] Filed: Aug. 1, 1974

[21] Appl. No.: 493,786

[52] U.S. Cl. .......................... 23/253 R; 23/253 A; 204/195 P; 137/255; 137/571; 137/572
[51] Int. Cl.² ...................... E03B 11/00; F17D 1/00; G01N 27/26; G01N 33/16
[58] Field of Search .......... 23/253 R, 230 B, 253 A, 23/230 A; 204/195 P; 137/255, 571, 572

[56] References Cited
UNITED STATES PATENTS

| | | |
|---|---|---|
| 3,582,284 | 6/1971 | Hamshere et al. ................ 23/253 R |
| 3,653,840 | 4/1972 | Silas .............................. 23/253 R X |
| 3,658,478 | 4/1972 | Spergel et al. ..................... 23/253 R |
| 3,763,422 | 10/1973 | MacPhee et al. ............. 23/230 B X |
| 3,854,877 | 12/1974 | Csaky et al. ................ 23/253 PC X |

*Primary Examiner*—Robert M. Reese

[57] ABSTRACT

A blood analysis system comprises a plurality of flow through measuring chambers, each of which has an associated measuring electrode system for producing an output signal as a function of a parameter of the blood sample in its measuring chamber; and a control device which in a first condition places the measuring chambers in fluid communication with the system inlet and in a second condition isolates the chambers to that the electrode systems may be calibrated concurrently and independently of one another

17 Claims, 13 Drawing Figures

ELECTROCHEMICAL ANALYSIS SYSTEM

SUMMARY OF INVENTION

This invention relates to apparatus for analysis of fluid samples and has particular application to apparatus for the analysis of parameters of precious fluids such as blood.

Frequently, an accurate measurement of two or more constituents of a fluid sample is desired. For example, the values of particular constituents of a blood sample may be useful in providing diagnostic information or for the control of life support devices. In particular instances pH, $PCO_2$ and $PO_2$ values of blood specimens provide important clinical information and analysis systems employing electrochemical electrodes have been developed for such analyses. Such systems generate electrical signals of very low magnitude and it is important to provide electrical stability in such systems to avoid introduction of potential sources of error. In order to maintain the desired accuracy of measurement it is necessary to calibrate such electrochemical electrode systems periodically, and different calibrating media are used for different electrode systems. For example, in a blood analysis instrument of the type shown in Spergel et al. U.S. Pat. No. 3,658,478, the carbon dioxide and oxygen sensors are calibrated with two gas mixtures, each of which contains known amounts of oxygen and carbon dioxide; and the pH electrode system is calibrated with two different buffer liquids. That system employs a sample inlet to the pH electrode system and a separate sample inlet to the carbon dioxide and oxygen measuring systems. A single inlet-plural measuring cell system permits induction of a sample in a single operation into the plurality of measuring cells and provides a convenience in operation as it reduces sample handling and assures that several parameter measurements on the single sample may be properly coordinated. Such an interconnection of measuring cells creates electrode calibration problems, however, where different calibrating media are used for different electrode systems. For example, a particular calibrating medium for use with one electrode system may have an adverse effect on another electrode system or the calibration thereof. Further, the time required for calibration of the several electrode systems may be considerably lengthened.

Accordingly, it is an object of the invention to provide a novel and improved fluid sample analysis instrument.

Another object of the invention is to provide a novel and improved calibration and measurement arrangement for a blood sample analysis instrument.

In accordance with the invention there is provided an electrochemical analysis system that includes a plurality of flow through measuring chambers, each measuring chamber having an inlet port and an outlet port, a system inlet port, conduit for connecting the system inlet port to both of the chambers, a calibrating fluid inlet port, and a control device having a first (sample) mode in which both the measuring chambers are in communication with the system inlet port and a second (calibrating) mode in which each measuring chamber is in communication with a distinct inlet port. The measuring chambers are isolated from one another in the second mode so that the electrode systems may be calibrated simulataneously with different calibrating media, one of the calibrating media being flowed through one measuring chamber but not through other chambers.

In one particular embodiment, the system has two measuring chambers disposed in a controlled temperature environment (e.g. a water bath) and includes four auxiliary inputs to which different calibrating fluids are supplied. A flow control device in a first mode channels a fluid sample to both measuring chambers; in a second mode channels calibrating fluid from one auxiliary input for flow through one measuring chamber while a separate flow path is established from a second auxiliary input for flow of a separate second calibrating fluid through the second measuring chamber; and in a third mode channels different calibrating fluids from the third and fourth auxiliary inputs to the measuring chambers. In another embodiment two auxiliary inputs are employed, the measuring chambers being connected in series in a first (analysis) mode and isolated from one another in a second (calibrating) mode. In the second mode, one chamber is vented to atmosphere while calibrating gas may be flowed through the other chamber from an auxiliary input to the system input. The control device in these embodiments is electrically inert and imposes no significant change between its modes (i.e. a change in electrical potential of less than 200 microvolts) in electrical influence on the electrochemical measuring systems. The invention enables analysis of samples of small fluid volume in arrangements which can be flushed easily and thoroughly and which are easily shiftable between different system modes for alternate calibration and measurement as desired.

Other objects, features and advantages of the invention will be seen as the following description of particular embodiments progresses, in conjunction with the drawings, in which:

DESCRIPTION OF PARTICULAR EMBODIMENTS

Figure 1:
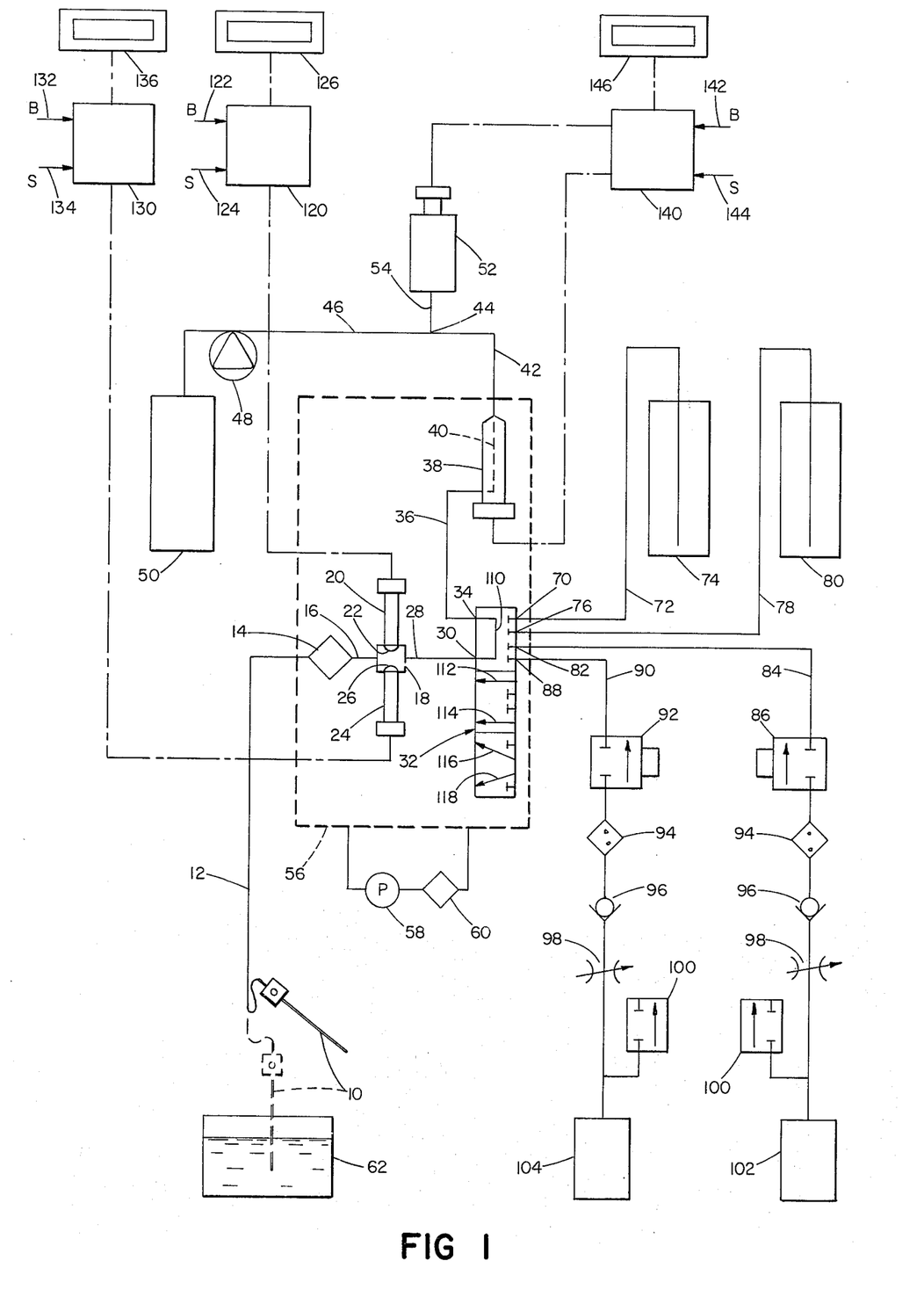
FIG. 1 is a diagram showing the fluid flow paths and interconnections employed in a blood analysis system constructed in accordance with the invention.

The blood gas analysis system shown diagramatically in FIG. 1 includes an inlet probe 10 through which a blood sample may be introduced into the system. Probe 10 is connected by conduit 12 to heater 14 and heater 14 is connected by conduit 16 to a first analysis chamber 18. Disposed in communication with chamber 18 is a $PO_2$ electrode 20 which employs a selectively permeable membrane 22 and produces a current, at a constant polarizing voltage that is directly proportional to the tension of oxygen diffusing through the membrane to the reactive cathode surface of the electrode 20.

Also in communication with chamber 18 is $PCO_2$ electrode 24 which includes a membrane 26 that is permeable to carbon dioxide gas but not to ions. The outlet of chamber 18 is connected by conduit 28 to port 30 of valve 32. A second port 34 of valve 32 is connected by conduit 36 to a pH electrode 38 that includes a capillary section measuring chamber 40 of pH sensitive glass through which the fluid sample flows. The outlet of measuring chamber 40 is connected by conduit 42 to a reference junction structure 44 and that reference junction structure is connected by conduit 46 through peristaltic pump 48 to waste receptacle 50. Reference electrode 52 which contains an electrolyte solution is connected by conduit 54 to the junction structure 44 to establish electrical contact between the reference electrode 52 and the sample in the capillary measuring chamber 40 of the pH electrode 38. Heater 14, electrodes 20, 24 and 38, valve 32, and measuring chambers 18 and 40 are disposed in chamber 56 through which water is circulated by pump 58 and controlled in temperature by thermostatically controlled heater 60.

The sample probe is movable between a first (sample receiving) position as indicated in FIG. 1 and a second position in which the probe tip is submerged in flush solution disposed in receptacle 62.

Valve 32 has a port 70 connected by a conduit 72 to a first buffer solution reservoir 74; a port 76 connected by conduit 78 to a second buffer solution reservoir 80; a third port 82 connected by conduit 84 to valve 86 and a fourth port 88 connected by conduit 90 to valve 92. Connected in series with each valve 86, 92 is a bubble chamber 94, a check valve 96, an adjustable needle valve 98 and a purge valve 100. The flow control system associated with valve 86 is connected to a first calibrating gas reservoir 102 and the flow system associated with valve 92 is connected to a second calibrating gas reservoir 104.

Valve 32 has three operative positions. In a first position, channel 110 connects port 30 to port 34 and ports 70, 76, 82 and 88 are blocked. In a second position, channel 112 connects port 70 to port 34 and channel 114 connects port 88 to port 30, ports 76 and 82 being blocked. In the third position, channel 116 connects port 76 to port 34 and channel 118 connects port 82 to port 30; ports 70 and 88 being blocked.

The electrical output signal from oxygen electrode 20 is applied to translating circuitry 120. That circuitry has a balance control input 122 and a slope control input 124 and its output is applied to digital display 126. The electrical output signal from carbon dioxide electrode 24 is applied to translating circuitry 130. That circuitry has a balance control input 132 and a slope control input 134 and its output is applied to digital display 136. The electrical outputs from pH electrode 38 and reference electrode 52 are applied to translating circuitry 140. That circuitry has a balance control input 142 and a slope control input 144 and its output is applied to digital display 146.

Figure 2:
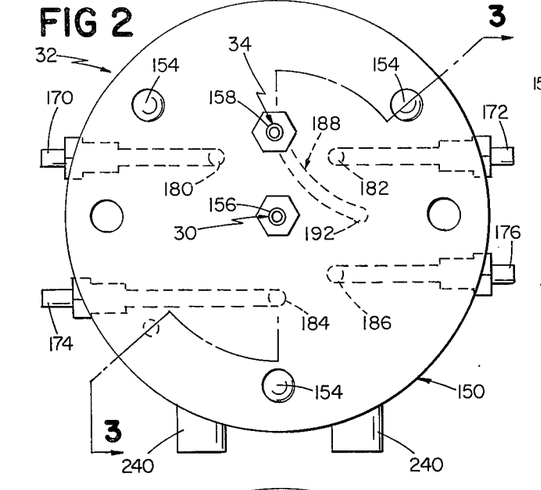
FIG. 2 is a bottom view of a valve employed in the system shown in FIG. 1.
Figure 3:
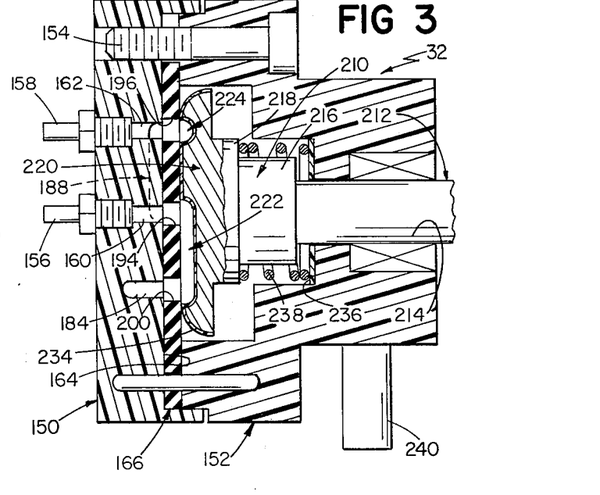
FIG. 3 is a sectional view of the valve taken along the line 3—3 of FIG. 2.

A particular valve 32 is shown in FIGS. 2 and 3. That valve includes a Delrin base 150, and a cap 152 secured together by bolts 154. Secured in base 150 are fittings 156, 158 which define ports 30 and 34, respectively, and communicate with ports 160, 162 in seat surface 164 of valve base 150. Fittings 170, 172, 174 and 176 define ports 70, 76, 82 and 88, respectively; fitting 170 communicating with a passage which defines port 180 in seat surface 164; fitting 172 communicating with a passage that defines port 182; fitting 174 communicating with a passage defining port 184; and fitting 176 communicating with a passage that terminates in port 186 in seat surface 164. Arcuate groove 188 extends from port 162 past port 182 to a termination in the 1½ centimeter diameter port circle 190 at point 192.

Figures 4, 5, 6:
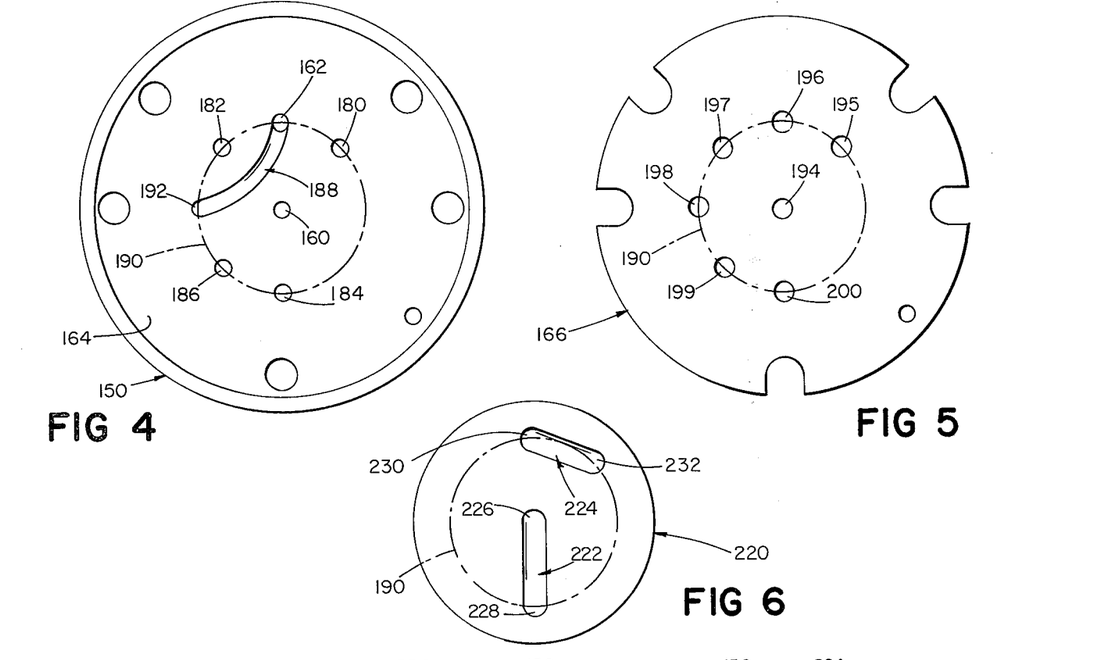
FIG. 4 is a top view of the valve base.
FIG. 5 is a top view of the sealing disc.
FIG. 6 is a bottom view of the selector disc.

Seated on surface 164 is a seal disc 166 of 50 Shore A Durometer neoprene rubber, the disc having a diameter of four centimeters and a thickness of 1½ millimeters. Formed in disc 166 as indicated in FIG. 5 are a set of seven passages 194–200 that are aligned with base ports 160, 180, 162, 182, 192, 186 and 184, respectively.

Sealing disc 166 is clamped on surface 164 by valve cap 152. Housed within cap 152 is a selector structure 210 that includes an outwardly extending shaft portion 212, bearing portion 214, collar 216, seat surface 218 and disc portion 220 that has two grooves 222, 224 formed in its face as indicated in FIG. 6. Groove 222 extends from the central point 226 to a point 228 in port circle 190; while groove 224 extends from point 230 on the port circle to a point 232 also on the port circle 190. Each groove has a cylindrical base of about ¾ millimeter radius. The surface of disc portion 220 has a Teflon coating 234.

Housed within cap, as indicated in FIG. 3, is a nylon washer 236 on which is seated spring 238 which biases the face of selector disc 220 against sealing disc 166.

Passages 240 extend into the valve cap 152 to permit circulation of tempering fluid therethrough.

Figure 7:
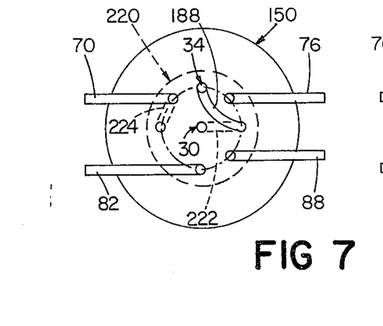
FIGS. 7, 8 and 9 are diagrammatic bottom views of the valve employed in the embodiment shown in FIG. 1 showing flow paths in three different valve positions.
Figure 8:
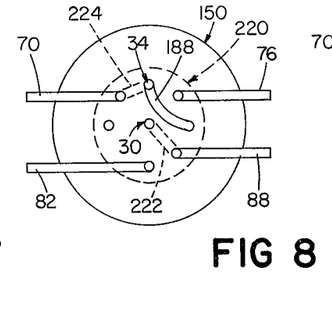
Figure 9:
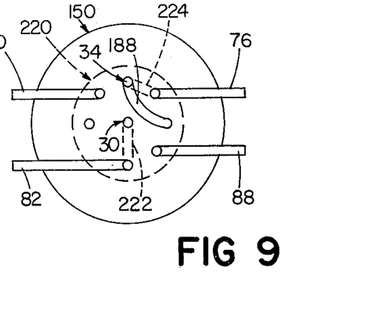

Diagrams of three aperture positions of the valve are shown in FIGS. 7–9. In the analysis position shown in FIG. 7, selector disc 220 is positioned so that radical groove 222 is in communication through seal disc port 198, with arcuate channel 188 completing a flow passage from port 30 (fitting 156), seal disc port 194, radially outwardly through groove 222 to arcuate channel 188 to port 196 and thence to port 34 (fitting 158). Valve ports 70, 76, 82 and 88 are all selected by selector disc 220 overlying corresponding ports 195, 197, 200 and 199, respectively, in seal disc 166.

In a first calibrating position shown in FIG. 8 (selector disc 220 being rotated 45°) radial groove 222 connects port 30 (via fitting 156 and seal disc port 194) to port 88 (seal disc port 199 and fitting 174); while tangential groove 224 connects port 34 (fitting 158 and seal disc port 196) to port 70 (seal disc port 195 and fitting 172); ports 76 and 82 remaining sealed by the interengagement of selector disc 220 and seal disc 166.

In the third position of the valve (shown in FIG. 9), a second calibrating position, selector disc 220 is rotated through a further 45° angle, placing port 30 in communication with port 82 through seal disc port 194, radial groove 222 and seal disc port 200; port 34 in communication with port 76 through seal disc port 196, tangent passage 224, and seal disc port 197; and sealing the remaining disc ports so that valve ports 70 and 88 are sealed.

In an analysis operation, valve 32 is in the position shown in FIG. 7, and a blood sample is introduced into measuring chambers 18 and 40 by operation of peristaltic pump 48. The tip of probe 10 is inserted into a container in which the sample is held and the sample is drawn through conduit 12, heater 14, measuring chamber 18, valve passage 110 (222 and 188), the second measuring chamber 40, and past reference junction 44. In this condition, the translating circuits 120, 130 and 140 may be released to respond to signals from electrodes 20, 24 and 38, respectively, and translate the electrical signals to output valves applied to the digital displays 126, 136 and 146, respectively. The oxygen electrode 20 produces a current which is directly proportional to the tension of oxygen diffusing through a membrane carried by the electrode assembly. Translating circuitry 120 responds to that current and translates that signal into an appropriate output for application to digital display 126. The carbon dioxide electrode assembly 24 is an adaption of a pH electrode system which senses carbon dioxide diffusing across a membrane and senses a resulting change in carbon dioxide concentration as a function of the change in pH of electrolyte and develops a voltage exponentially related to PCO2. This output voltage is translated by circuitry 130 into an output signal which is applied to digital display 136. The pH electrode system 38 includes a capillary of pH sensitive glass through which the blood sample is drawn. A potential difference between the surfaces of the glass membrane is proportional to the differences in pH and this potential difference is applied to translating circuitry 140 which generates an output that is applied to digital display 146.

In preparation for such an analysis, the oxygen and carbon dioxide sensors 20, 24 are calibrated with two gases from sources 102 and 104, and the pH sensor 38 is calibrated with buffer liquids from sources 74 and 80. With the valve 32 in the analysis position (FIG. 7) and with sample tip 10 immersed in flush solution in reservoir 62, peristaltic pump 48 is operated to draw flush solution through the system in a cleaning operation. Valve 32 is then moved to a first calibration position (FIG. 8) in which measuring chamber 18 is connected to gas source 104 and pH measuring chamber 40 is connected to high buffer (pH 7.384) source 74. In this valve position, the gas flowing through measuring chamber 18 has a mixture of about five percent carbon dioxide, twelve percent oxygen and the balance nitrogen, and the carbon dioxide electrode translating circuitry 132 is adjusted by balance control 132 in a zeroing operation. The pH circuitry 140 is also adjusted by balance control 142 in a zeroing operation. After the pH and carbon dioxide electrode systems are zeroed, the valve is moved to the third position (FIG. 9) in which position a gas (about ten percent carbon dioxide, no oxygen and the remainder nitrogen) from source 102 is applied to measuring chamber 18 and the low buffer (pH 6.84) source 80 is connected to measuring chamber 40. Peristaltic pump 48 is operated to place the low buffer in chamber 40. In this valve position, the oxygen electrode circuitry 120 balance control 122 is adjusted with the calibrating gas from source 102. At the same time the carbon dioxide translating circuitry 130 is sloped (through adjustment of slope control 134) and the pH electrode system circuitry 140 is sloped through adjustment of slope control 144. After the oxygen system has been zeroed and the carbon dioxide and pH electrode systems have been adjusted for slope, valve 32 is returned to its first calibrating position (FIG. 8) and a slope adjustment for the oxygen system is made utilizing the calibrating gas from source 104. In each calibration measurement, the appropriate valve 86, 92 is opened and the selected calibration gas flows under pressure from its source through adjustable needle valve 98, check valve 96, bubble chamber 94, measuring chamber 18, heater 14 and out sample tip 10 into the flush solution in reservoir 62 for release to the atmosphere.

When the response of the electrode systems have been satisfactorily calibrated, valve 32 is moved to the analysis position (FIG. 7) and the instrument is ready for an analysis sequence. As above discussed, sample tip 10 is removed from the flush solution and immersed in a blood sample to be analyzed, pump 48 is operated to induct about 500 microliters of blood through the preheater 14 into measuring chambers 18 and 40 and past the liquid junction 44. After the sample has been so flowed into those chambers, the translating circuits are energized and measurements of pH, $PCO_2$ and $PO_2$ are simultaneously obtained on that sample. The sample tip 10 is replaced in the flush solution and after the analysis values are displayed, the sample is flushed from the measuring chambers 18 and 40 by operation of pump 48, flush solution being drawn through the system in a cleaning operation. Calibration of the electrode systems may be periodically checked by placing the valve in a calibrate position and allowing the selected calibrating gas to flow through chamber 18 and pumping the selected buffer liquid through chamber 40, the displays being released so that the operator may check instrument balance.

Figure 10:
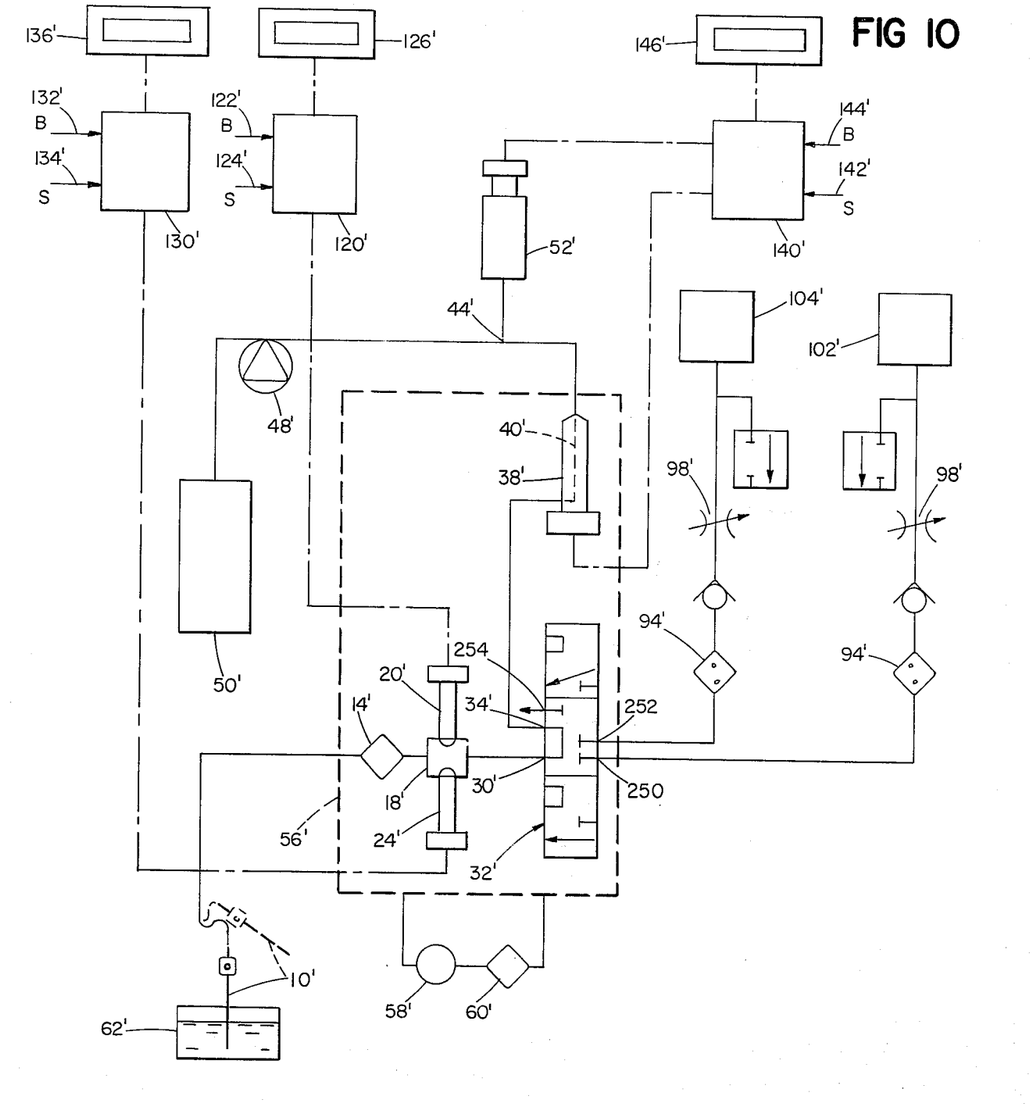
FIG. 10 is a diagram showing fluid flow paths and interconnections in a second blood analysis system constructed in accordance with the invention.

A second embodiment is illustrated in FIG. 10. In this embodiment, components that are similar to the components shown in FIG. 1 are identified with primed reference numerals. Thus the system includes measuring chamber 18' with oxygen electrode 20' and carbon dioxide electrode 24' coupled to it, and measuring chamber 40' is employed in a pH electrode system. Valve 32' is also a three-position valve and has a port 30' connected to chamber 18' and a second port 34' connected to chamber 40'. A third port 250 is connected through bubble chamber 94' and an adjustable needle valve 98' to source of calibrating gas 102'; a fourth port 252 is similarly connected to a second source of calibrating gas 104'; and a vent port 254 connected to atmosphere.

Figure 11:
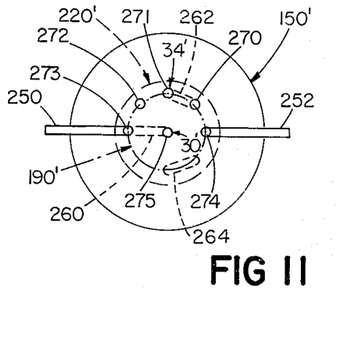
FIGS. 11, 12 and 13 are diagrammatic views showing flow paths in three different positions of the valve employed in the embodiment shown in FIG. 10.
Figure 12:
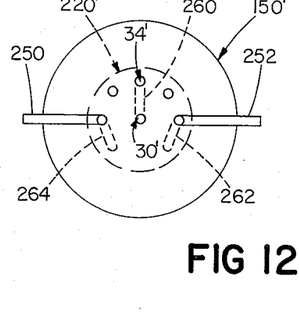
Figure 13:
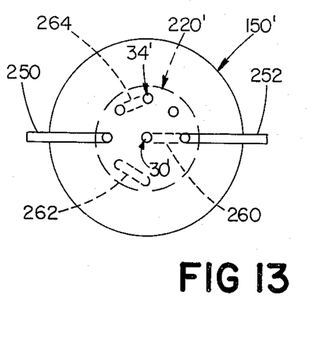

Valve 32' in a particular embodiment is also a face valve which has a selector disc 220' in which (as indicated in FIGS. 11–13) is formed a radial groove 260 and two tangential grooves 262, 264. The cooperating sealing disc 166' has a series of ports 270–274 arranged in a part circle 190', port 270 being coupled to atmosphere (valve port 254); port 271 being coupled to port 34'; port 272 also being coupled to atmosphere; port 273 being connected to valve port 250; and port 274 being connected to valve port 252; and a central port 275 connected to port 30'.

The valve has three selector disc positions offset from one another by 90°. In a first calibrate position indicated in FIG. 11, tangential groove 262 connects port 34' to the vent port 270 and radial groove 260 connects valve port 250 to port 30'. In a second angular position (FIG. 12) radial groove 260 connects ports 30' and 34' in an aspirate or flush configuration in which measuring chambers 18' and 40' are connected in series. In a second calibrate position (FIG. 13) radial groove 260 connects port 30' to the valve port 252 and tangential passage 264 connects port 34' to atmosphere.

In this system, the calibrating liquids for the pH electrode system are introduced through the sample tip 10' while the valve 32' is in the aspirate position (FIG. 12). Thus, with the valve in the aspirate position, a low buffer is placed in measuring chamber 40' and leak junction 44'. The valve is then moved to one of the calibrate positions, for example the position in FIG. 11. In this position the pH measuring chamber 40 is vented to atmosphere as circuitry 140' may be balanced; and the twelve percent carbon dioxide zero percent oxygen gas may be flowed through the measuring chamber 18' permitting the oxygen system to be balanced. After the oxygen and pH measuring systems have been balanced, the valve 32' is again shifted to the aspirate position and the buffer is flushed from chamber 40' and replaced by a second calibrating buffer. The valve is then moved to the alternate calibrate position (FIG. 13) where port 34' is again vented to atmosphere and a second calibrating gas from source 104' may be flowed through chamber 18', again forcing the buffer from that chamber and allowing a calibration procedure to balance the carbon dioxide electrode system and to slope the oxygen electrode system. At this time the pH slope of the pH electrode system is adjusted. After these adjustments are completed, the valve is moved back to the first calibrating position (FIG. 11) and the carbon dioxide electrode system slope is adjusted. The valve is then again placed in the aspirate position (FIG. 12), the buffer is drawn out of the measuring chambers 18' and 40' and those chambers are filled with flush solution in standby condition awaiting initiation of an analysis sequence.

It will be apparent that other valving configurations and calibrating sequences may be employed. The valve may be operated automatically or manually. In use of the embodiment of FIGS. 10–13 the calibrating buffers and gases should be selected to insure that no adverse interaction or equilibration delay occurs. In general, it is preferred to use a fully isolated system, for example of the type shown in FIGS. 1–9.

While particular embodiments of the invention have been shown and described, it is not intended that the invention be limited to the disclosed embodiments or to details thereof and departures may be made therefrom within the spirit and scope of the invention as defined in the claims.

What is claimed is:

1. An electrochemical analysis system comprising a plurality of flow through measuring chambers, a measuring electrode system connected in measuring relation to each said chamber,
   system inlet port structure, conduit connecting said system inlet port structure to said chambers, calibrating fluid inlet port structure, and
   a fluid control having a first (analysis) mode in which said measuring chambers are in fluid communication with the system inlet port structure so that fluid from the same sample may be concurrently flowed into said measuring chambers for concurrent sensing by said measuring electrode systems, and a second mode in which one measuring chamber is in fluid communication with said calibrating fluid inlet port structure and said measuring chambers are in fluid isolation from one another so that the electrode systems may be calibrated concurrently and independently of one another.

2. The system as claimed in claim 1 wherein said measuring chambers are disposed in a controlled temperature environment (e.g. a water bath).

3. The system as claimed in claim 1 wherein there are two measuring chambers and said fluid control has four auxiliary inputs to which different calibrating fluids are supplied, said fluid control in said first mode channelling a fluid sample from said system inlet port structure to both measuring chambers; in said second mode channelling calibrating fluid from one auxiliary input for flow through one measuring chamber while a separate flow path is established from a secondary auxiliary input for flow of a separate second calibrating fluid through the second measuring chamber; and in a third mode channelling different calibrating fluids from third and fourth auxiliary inputs to said measuring chambers.

4. The system as claimed in claim 1 wherein said fluid control has an auxiliary input, said measuring chambers being connected in series fluid communication in said first (analysis) mode and in fluid isolation from one another in said second (calibrating) mode, said fluid control in said second mode venting one chamber to atmosphere while permitting calibrating fluid to be flowed through the other chamber from said auxiliary input to said system inlet port structure.

5. The system as claimed in claim 1 wherein said fluid control is electrically inert and imposes a change in electrical influence on said electrochemical measuring systems between said first and second modes of less than 200 microvolts.

6. A precious fluid analysis system comprising:
   a plurality of flow through measuring chambers,
   a plurality of measuring electrode systems, each said measuring electrode system being coupled to a respective measuring chamber for producing an output signal as a function of a parameter of a precious fluid sample in said respective chamber,
   system inlet port structure, conduit connecting said system inlet port structure to said chambers, and
   a fluid control having a first condition in which said measuring chambers are in fluid communication with the system inlet port structure so that fluid from the same sample may be concurrently flowed into said measuring chambers for concurrent sensing by said measuring electrode systems, and a second condition in which said measuring chambers are in fluid isolation from one another so that the electrode systems may be calibrated concurrently and independently of one another.

7. The system as claimed in claim 6 and further including temperature control structure for stabilizing the temperature of said measuring chambers and said control device.

8. The system as claimed in claim 6 wherein said fluid control is movable from said first condition to said second condition without significant change in electrical influence on said measuring electrode systems.

9. The system as claimed in claim 6 wherein a first measuring system is connected to measure a gaseous parameter of the fluid sample in a first measuring chamber, and a second measuring system is connected to measure the pH of the fluid sample in a second measuring chamber, said system inlet port structure is connected to said first measuring chamber, and said fluid control is connected between said first and second measuring chambers.

10. The system as claimed in claim 6 wherein said fluid control has an auxiliary input, said measuring chambers being connected in series in said first condition and isolated from one another in said second condition, said fluid control in said second condition permitting calibrating fluid to be flowed through one chamber from said auxiliary input.

11. The system as claimed in claim 6 wherein a first measuring system is connected to measure a gaseous parameter of blood in a first measuring chamber, and a second measuring system is connected to measure the pH of blood in a second measuring chamber, and said fluid control is movable between a first condition for channelling a blood sample to said first and second measuring chambers for analysis and a second condition in which a first flow path is established for flow of a gaseous parameter calibrating fluid to said first chamber for use in calibration of said first measuring system and a separate second flow path is established for flow of a separate pH calibrating fluid to said second chamber for calibration of said second measuring system, the movement of said fluid control between said first and second conditions imposing no significant change in electrical influence on said first and second measuring systems.

12. The system as claimed in claim 6 wherein said fluid control is a valve having a sealing member in which a plurality of spaced ports are defined, a selector member having a plurality of channels for selectively connecting ports of said sealing member together, the surface of said selector member being in sealing engagement with said sealing member, and control means for shifting the position of said sealing and selector members relative to one another to change the ports of said sealing member that are connected by channels of said selector member.

13. The system as claimed in claim 12 wherein said sealing member is a planar member of resilient material and said selector member has a smooth surface of low frictional resistance, and further including means biasing said smooth surface into sealing engagement with said sealing member.

14. The system as claimed in claim 13 wherein said valve has four auxiliary inputs to which different calibrating fluids are supplied, said valve being movable between a first position for channelling a fluid sample to said measuring chambers; a second position for channelling calibrating fluid from one auxiliary input for flow through one measuring chamber while a separate flow path is established from a second auxiliary input for flow of a separate second calibrating fluid through the second measuring chamber; and a third position for channelling different calibrating fluids from the third and fourth auxiliary inputs to said measuring chambers.

15. The system as claimed in claim 14 and further including a temperature stabilizing chamber in which said measuring chambers and said valve are disposed.

16. The system as claimed in claim 15 wherein said control device is a valve and the movement of said valve from said first position to said second position produces a change of less than two hundred microvolts on said measuring electrode systems.

17. The system as claimed in claim 16 wherein a first measuring system is connected to measure a gaseous parameter of blood in a first measuring chamber, and a second measuring system is connected to measure the pH of blood in a second measuring chamber, said system inlet port structure is connected to said first measuring chamber, a system discharge port is connected to said second measuring chamber, and said valve is connected between said first and second measuring chambers.

* * * * *

UNITED STATES PATENT OFFICE
CERTIFICATE OF CORRECTION

Patent No. 3,960,498  Dated June 1, 1976

Inventor(s) Jerrold Zindler et al.  Page 1 of 2

It is certified that error appears in the above-identified patent and that said Letters Patent are hereby corrected as shown below:

On the cover sheet the illustrative drawing should appear as shown on the attached sheet.

Column 4, line 30, "aperture" should read -- operative --.

Column 4, line 32, "radical" should read -- radial --.

Column 5, line 1, "valves" shuuld read -- values --.

Column 7, line 53, after "second" insert -- (calibrating) --.

Signed and Sealed this

Thirtieth Day of November 1976

[SEAL]

Attest:

RUTH C. MASON  
Attesting Officer

C. MARSHALL DANN  
Commissioner of Patents and Trademarks